| (12) | United States Patent | (10) Patent No.: | US 9,605,249 B2 |
|---|---|---|---|
| | Mitsuzawa et al. | (45) Date of Patent: | Mar. 28, 2017 |

(54) METHOD FOR PRODUCING HIGHLY ACTIVE CELLOBIOHYDROLASE AND HIGHLY ACTIVE CELLOBIOHYDROLASE

(71) Applicant: HONDA MOTOR CO., LTD., Tokyo (JP)

(72) Inventors: Shigenobu Mitsuzawa, Saitama (JP); Keiichi Kimura, Saitama (JP); Maiko Tanaka, Saitama (JP); Satoru Shinkawa, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 14/957,915

(22) Filed: Dec. 3, 2015

(65) Prior Publication Data

US 2016/0160200 A1 Jun. 9, 2016

(30) Foreign Application Priority Data

Dec. 4, 2014 (JP) ................................ 2014-246121

(51) Int. Cl.
*C12N 9/24* (2006.01)
*C12N 9/42* (2006.01)

(52) U.S. Cl.
CPC .... *C12N 9/2437* (2013.01); *C12Y 302/01091* (2013.01)

(58) Field of Classification Search
CPC .................................................. C12N 9/2437
See application file for complete search history.

(56) References Cited

U.S. PATENT DOCUMENTS

| 8,790,894 B2 | 7/2014 | Van Der Laan et al. |
| 2013/0309729 A1 | 11/2013 | Van Der Laan et al. |

FOREIGN PATENT DOCUMENTS

| EP | 2 357 227 A1 | 8/2011 |
| JP | 2010-046034 | 3/2010 |

OTHER PUBLICATIONS

"Glycoside Hydrolase Families" in CAZypedia, available at URL https://www.cazypedia.org/index.php/Glycoside_Hydrolase_Families, accessed Aug. 16, 2016.*
European Search Report dated Apr. 14, 2016.

* cited by examiner

*Primary Examiner* — Suzanne M Noakes
(74) *Attorney, Agent, or Firm* — Rankin, Hill & Clark LLP (57) ABSTRACT

An object of the invention is to provide cellobiohydrolase with high activity. The activity of cellobiohydrolase can be improved by substituting, with alanine, asparagine that is the amino acid at position 62 from the N-terminal of cellobiohydrolase shown in SEQ ID NO: 1, or asparagine at a position corresponding to the position 62 in an amino acid sequence corresponding to the sequence of the cellobiohydrolase shown in SEQ ID NO: 1.

1 Claim, 3 Drawing Sheets

SEQUENCE LISTING

```
<160> NUMBER OF SEQ ID NOS: 36

<210> SEQ ID NO 1
<211> LENGTH: 529
<212> TYPE: PRT
<213> ORGANISM: Acremonium cellulolyticus

<400> SEQUENCE: 1

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Ser Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
```

```
            115                 120                 125
Arg Thr Tyr Leu Met Ala Asp Asn Thr His Tyr Gln Ile Phe Asp Leu
            130                 135                 140
Leu Asn Gln Glu Phe Thr Phe Thr Val Asp Val Ser His Leu Pro Cys
145                 150                 155                 160
Gly Leu Asn Gly Ala Leu Tyr Phe Val Thr Met Asp Ala Asp Gly Gly
                    165                 170                 175
Val Ser Lys Tyr Pro Asn Asn Lys Ala Gly Ala Gln Tyr Gly Val Gly
                    180                 185                 190
Tyr Cys Asp Ser Gln Cys Pro Arg Asp Leu Lys Phe Ile Ala Gly Gln
                    195                 200                 205
Ala Asn Val Glu Gly Trp Thr Pro Ser Ser Asn Asn Ala Asn Thr Gly
210                 215                 220
Ile Gly Asn His Gly Ala Cys Cys Ala Glu Leu Asp Ile Trp Glu Ala
225                 230                 235                 240
Asn Ser Ile Ser Glu Ala Leu Thr Pro His Pro Cys Asp Thr Pro Gly
                    245                 250                 255
Leu Ser Val Cys Thr Thr Asp Ala Cys Gly Gly Thr Tyr Ser Ser Asp
                    260                 265                 270
Arg Tyr Ala Gly Thr Cys Asp Pro Asp Gly Cys Asp Phe Asn Pro Tyr
                    275                 280                 285
Arg Leu Gly Val Thr Asp Phe Tyr Gly Ser Gly Lys Thr Val Asp Thr
                    290                 295                 300
Thr Lys Pro Phe Thr Val Val Thr Gln Phe Val Thr Asn Asp Gly Thr
305                 310                 315                 320
Ser Thr Gly Ser Leu Ser Glu Ile Arg Arg Tyr Tyr Val Gln Asn Gly
                    325                 330                 335
Val Val Ile Pro Gln Pro Ser Ser Lys Ile Ser Gly Ile Ser Gly Asn
                    340                 345                 350
Val Ile Asn Ser Asp Tyr Cys Ala Ala Glu Ile Ser Thr Phe Gly Gly
                    355                 360                 365
Thr Ala Ser Phe Ser Lys His Gly Gly Leu Thr Asn Met Ala Ala Gly
                    370                 375                 380
Met Glu Ala Gly Met Val Leu Val Met Ser Leu Trp Asp Asp Tyr Ala
385                 390                 395                 400
Val Asn Met Leu Trp Leu Asp Ser Thr Tyr Pro Thr Asn Ala Thr Gly
                    405                 410                 415
Thr Pro Gly Ala Ala Arg Gly Thr Cys Ala Thr Thr Ser Gly Asp Pro
                    420                 425                 430
Lys Thr Val Glu Ala Gln Ser Gly Ser Ser Tyr Val Thr Phe Ser Asp
                    435                 440                 445
Ile Arg Val Gly Pro Phe Asn Ser Thr Phe Ser Gly Gly Ser Ser Thr
                    450                 455                 460
Gly Gly Ser Thr Thr Thr Thr Ala Ser Arg Thr Thr Thr Thr Ser Ala
465                 470                 475                 480
Ser Ser Thr Ser Thr Ser Ser Thr Ser Thr Gly Thr Gly Val Ala Gly
                    485                 490                 495
His Trp Gly Gln Cys Gly Gly Gln Gly Trp Thr Gly Pro Thr Thr Cys
                    500                 505                 510
Val Ser Gly Thr Thr Cys Thr Val Val Asn Pro Tyr Tyr Ser Gln Cys
                    515                 520                 525
Leu
```

```
<210> SEQ ID NO 2
<211> LENGTH: 529
<212> TYPE: PRT
<213> ORGANISM: Acremonium cellulolyticus

<400> SEQUENCE: 2

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
                20                  25                  30

Ala Glu Thr His Pro Ser Leu Ser Trp Ser Thr Cys Lys Ser Gly Gly
                35                  40                  45

Ser Cys Thr Thr Asn Ser Gly Ala Ile Thr Leu Asp Ala Ala Trp Arg
        50                  55                  60

Trp Val His Gly Val Asn Thr Ser Thr Asn Cys Tyr Thr Gly Asn Thr
65                  70                  75                  80

Trp Asn Ser Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
                100                 105                 110

Gly Asn Ser Leu Arg Leu Asn Phe Val Thr Gly Ser Asn Val Gly Ser
                115                 120                 125

Arg Thr Tyr Leu Met Ala Asp Asn Thr His Tyr Gln Ile Phe Asp Leu
                130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
                180                 185                 190

Tyr Cys Asp Ser Gln Cys Pro Arg Asp Leu Lys Phe Ile Ala Gly Gln
                195                 200                 205

Ala Asn Val Glu Gly Trp Thr Pro Ser Ser Asn Asn Ala Asn Thr Gly
                210                 215                 220

Ile Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
                260                 265                 270

Arg Tyr Ala Gly Thr Cys Asp Pro Asp Gly Cys Asp Phe Asn Pro Tyr
                275                 280                 285

Arg Leu Gly Val Thr Asp Phe Tyr Gly Ser Gly Lys Thr Val Asp Thr
                290                 295                 300

Thr Lys Pro Phe Thr Val Val Thr Gln Phe Val Thr Asn Asp Gly Thr
305                 310                 315                 320

Ser Thr Gly Ser Leu Ser Glu Ile Arg Arg Tyr Tyr Val Gln Asn Gly
                325                 330                 335

Val Val Ile Pro Gln Pro Ser Ser Lys Ile Ser Gly Ile Ser Gly Asn
                340                 345                 350

Val Ile Asn Ser Asp Tyr Cys Ala Ala Glu Ile Ser Thr Phe Gly Gly
                355                 360                 365

Thr Ala Ser Phe Ser Lys His Gly Gly Leu Thr Asn Met Ala Ala Gly
                370                 375                 380
```

Met Glu Ala Gly Met Val Leu Val Met Ser Leu Trp Asp Asp Tyr Ala
385                 390                 395                 400

Val Asn Met Leu Trp Leu Asp Ser Thr Tyr Pro Thr Asn Ala Thr Gly
            405                 410                 415

Thr Pro Gly Ala Ala Arg Gly Thr Cys Ala Thr Thr Ser Gly Asp Pro
        420                 425                 430

Lys Thr Val Glu Ala Gln Ser Gly Ser Ser Tyr Val Thr Phe Ser Asp
            435                 440                 445

Ile Arg Val Gly Pro Phe Asn Ser Thr Phe Ser Gly Gly Ser Ser Thr
        450                 455                 460

Gly Gly Ser Thr Thr Thr Thr Ala Ser Arg Thr Thr Thr Thr Ser Ala
465                 470                 475                 480

Ser Ser Thr Ser Thr Ser Ser Thr Ser Thr Gly Thr Gly Val Ala Gly
            485                 490                 495

His Trp Gly Gln Cys Gly Gly Gln Gly Trp Thr Gly Pro Thr Thr Cys
        500                 505                 510

Val Ser Gly Thr Thr Cys Thr Val Val Asn Pro Tyr Tyr Ser Gln Cys
            515                 520                 525

Leu

<210> SEQ ID NO 3
<211> LENGTH: 36
<212> TYPE: DNA
<213> ORGANISM: Artificial Sequence
<220> FEATURE:
<223> OTHER INFORMATION: CBH

<400> SEQUENCE: 3
tcctccaagt tacccatgtc tgccttgaac tctttc                         36

<210> SEQ ID NO 4
<211> LENGTH: 40
<212> TYPE: DNA
<213> ORGANISM: Artificial Sequence
<220> FEATURE:
<223> OTHER INFORMATION: CBH

<400> SEQUENCE: 4
cgcttcgtcg accccctaca aacattgaga gtagtaaggg                     40

<210> SEQ ID NO 5
<211> LENGTH: 32
<212> TYPE: DNA
<213> ORGANISM: Artificial Sequence
<220> FEATURE:
<223> OTHER INFORMATION: niaD

<400> SEQUENCE: 5
atgctcggga gctttggatt tcctacgtct tc                             32

<210> SEQ ID NO 6
<211> LENGTH: 33
<212> TYPE: DNA
<213> ORGANISM: Artificial Sequence
<220> FEATURE:
<223> OTHER INFORMATION: niaD

<400> SEQUENCE: 6
atgcatatgt cgagagtgtt gtgtgggtca acg                            33

<210> SEQ ID NO 7
<211> LENGTH: 33
<212> TYPE: DNA
<213> ORGANISM: Artificial Sequence
<220> FEATURE:
<223> OTHER INFORMATION: agdA

<400> SEQUENCE: 7
atggtcgacg aagcgtaaca ggatagccta gac                          33

<210> SEQ ID NO 8
<211> LENGTH: 33
<212> TYPE: DNA
<213> ORGANISM: Artificial Sequence
<220> FEATURE:
<223> OTHER INFORMATION: agdA

<400> SEQUENCE: 8
atgcccgaga gtaacccatt cccggttctc tag                          33

<210> SEQ ID NO 9
<211> LENGTH: 30
<212> TYPE: DNA
<213> ORGANISM: Artificial Sequence
<220> FEATURE:
<223> OTHER INFORMATION: enoA

<400> SEQUENCE: 9
atggctagca gatctcgcgg cagggttgac                              30

<210> SEQ ID NO 10
<211> LENGTH: 40
<212> TYPE: DNA
<213> ORGANISM: Artificial Sequence
<220> FEATURE:
<223> OTHER INFORMATION: enoA

<400> SEQUENCE: 10
atggtcgacc ccgggtaact tggaggacgg aagaaaagag                   40

<210> SEQ ID NO 11
<211> LENGTH: 30
<212> TYPE: DNA
<213> ORGANISM: Artificial Sequence
<220> FEATURE:
<223> OTHER INFORMATION: K203A

<400> SEQUENCE: 11
gatgaaggcc aagtcacgag ggcattgaga                              30

<210> SEQ ID NO 12
<211> LENGTH: 30
<212> TYPE: DNA
<213> ORGANISM: Artificial Sequence
<220> FEATURE:
<223> OTHER INFORMATION: N062A

<400> SEQUENCE: 12
acgccaggcg gcatctaacg taatggcacc                              30

<210> SEQ ID NO 13
<211> LENGTH: 30
<212> TYPE: DNA
<213> ORGANISM: Artificial Sequence
<220> FEATURE:
<223> OTHER INFORMATION: N125A

<400> SEQUENCE: 13
tccgacggcg gaaccggtaa cgaagttcag                                               30

<210> SEQ ID NO 14
<211> LENGTH: 30
<212> TYPE: DNA
<213> ORGANISM: Artificial Sequence
<220> FEATURE:
<223> OTHER INFORMATION: D201A

<400> SEQUENCE: 14
cttcaaggca cgagggcatt gagagtcaca                                               30

<210> SEQ ID NO 15
<211> LENGTH: 30
<212> TYPE: DNA
<213> ORGANISM: Artificial Sequence
<220> FEATURE:
<223> OTHER INFORMATION: R289A

<400> SEQUENCE: 15
accaagggcg taagggttga agtcacatcc                                               30

<210> SEQ ID NO 16
<211> LENGTH: 30
<212> TYPE: DNA
<213> ORGANISM: Artificial Sequence
<220> FEATURE:
<223> OTHER INFORMATION: D281A

<400> SEQUENCE: 16
acatccggca gggtcgcagg taccggcgta                                               30

<210> SEQ ID NO 17
<211> LENGTH: 30
<212> TYPE: DNA
<213> ORGANISM: Artificial Sequence
<220> FEATURE:
<223> OTHER INFORMATION: K203A

<400> SEQUENCE: 17
gacttggcct tcatcgctgg tcaggccaac                                               30

<210> SEQ ID NO 18
<211> LENGTH: 30
<212> TYPE: DNA
<213> ORGANISM: Artificial Sequence
<220> FEATURE:
<223> OTHER INFORMATION: N062A

<400> SEQUENCE: 18
gatgccgcct ggcgttgggt ccatggtgtc                                               30

<210> SEQ ID NO 19
<211> LENGTH: 30
<212> TYPE: DNA
<213> ORGANISM: Artificial Sequence
<220> FEATURE:
<223> OTHER INFORMATION: N125A

<400> SEQUENCE: 19
ggttccgccg tcggatctcg tacttacctg                                               30

<210> SEQ ID NO 20
<211> LENGTH: 30

<210> SEQ ID NO 20
<211> LENGTH: 30
<212> TYPE: DNA
<213> ORGANISM: Artificial Sequence
<220> FEATURE:
<223> OTHER INFORMATION: D201A

<400> SEQUENCE: 20
cctcgtgcct tgaagttcat cgctggtcag                                30

<210> SEQ ID NO 21
<211> LENGTH: 30
<212> TYPE: DNA
<213> ORGANISM: Artificial Sequence
<220> FEATURE:
<223> OTHER INFORMATION: R289A

<400> SEQUENCE: 21
ccttacgccc ttggtgtcac tgacttctac                                30

<210> SEQ ID NO 22
<211> LENGTH: 30
<212> TYPE: DNA
<213> ORGANISM: Artificial Sequence
<220> FEATURE:
<223> OTHER INFORMATION: D281A

<400> SEQUENCE: 22
gaccctgccg gatgtgactt caaccttac                                 30

<210> SEQ ID NO 23
<211> LENGTH: 30
<212> TYPE: DNA
<213> ORGANISM: Artificial Sequence
<220> FEATURE:
<223> OTHER INFORMATION: N062W

<400> SEQUENCE: 23
acgccaccag gcatctaacg taatggcacc                                30

<210> SEQ ID NO 24
<211> LENGTH: 30
<212> TYPE: DNA
<213> ORGANISM: Artificial Sequence
<220> FEATURE:
<223> OTHER INFORMATION: N062V

<400> SEQUENCE: 24
acgccagacg gcatctaacg taatggcacc                                30

<210> SEQ ID NO 25
<211> LENGTH: 30
<212> TYPE: DNA
<213> ORGANISM: Artificial Sequence
<220> FEATURE:
<223> OTHER INFORMATION: N062S

<400> SEQUENCE: 25
acgccaggag gcatctaacg taatggcacc                                30

<210> SEQ ID NO 26
<211> LENGTH: 30
<212> TYPE: DNA
<213> ORGANISM: Artificial Sequence
<220> FEATURE:
<223> OTHER INFORMATION: N062Q

<400> SEQUENCE: 26
acgccactgg gcatctaacg taatggcacc                    30

<210> SEQ ID NO 27
<211> LENGTH: 30
<212> TYPE: DNA
<213> ORGANISM: Artificial Sequence
<220> FEATURE:
<223> OTHER INFORMATION: N062E

<400> SEQUENCE: 27
acgccactcg gcatctaacg taatggcacc                    30

<210> SEQ ID NO 28
<211> LENGTH: 30
<212> TYPE: DNA
<213> ORGANISM: Artificial Sequence
<220> FEATURE:
<223> OTHER INFORMATION: N062K

<400> SEQUENCE: 28
acgccacttg gcatctaacg taatggcacc                    30

<210> SEQ ID NO 29
<211> LENGTH: 30
<212> TYPE: DNA
<213> ORGANISM: Artificial Sequence
<220> FEATURE:
<223> OTHER INFORMATION: N062H

<400> SEQUENCE: 29
acgccaatgg gcatctaacg taatggcacc                    30

<210> SEQ ID NO 30
<211> LENGTH: 30
<212> TYPE: DNA
<213> ORGANISM: Artificial Sequence
<220> FEATURE:
<223> OTHER INFORMATION: N062W

<400> SEQUENCE: 30
gatgcctggt ggcgttgggt ccatggtgtc                    30

<210> SEQ ID NO 31
<211> LENGTH: 30
<212> TYPE: DNA
<213> ORGANISM: Artificial Sequence
<220> FEATURE:
<223> OTHER INFORMATION: N062V

<400> SEQUENCE: 31
gatgccgtct ggcgttgggt ccatggtgtc                    30

<210> SEQ ID NO 32
<211> LENGTH: 30
<212> TYPE: DNA
<213> ORGANISM: Artificial Sequence
<220> FEATURE:
<223> OTHER INFORMATION: N062S

<400> SEQUENCE: 32
gatgcctcct ggcgttgggt ccatggtgtc                    30

<210> SEQ ID NO 33
<211> LENGTH: 30
<212> TYPE: DNA
<213> ORGANISM: Artificial Sequence

```
<220> FEATURE:
<223> OTHER INFORMATION: N062Q

<400> SEQUENCE: 33
gatgcccagt ggcgttgggt ccatggtgtc                              30

<210> SEQ ID NO 34
<211> LENGTH: 30
<212> TYPE: DNA
<213> ORGANISM: Artificial Sequence
<220> FEATURE:
<223> OTHER INFORMATION: N062E

<400> SEQUENCE: 34
gatgccgagt ggcgttgggt ccatggtgtc                              30

<210> SEQ ID NO 35
<211> LENGTH: 30
<212> TYPE: DNA
<213> ORGANISM: Artificial Sequence
<220> FEATURE:
<223> OTHER INFORMATION: N062K

<400> SEQUENCE: 35
gatgccaagt ggcgttgggt ccatggtgtc                              30

<210> SEQ ID NO 36
<211> LENGTH: 30
<212> TYPE: DNA
<213> ORGANISM: Artificial Sequence
<220> FEATURE:
<223> OTHER INFORMATION: N062H

<400> SEQUENCE: 36
gatgcccatt ggcgttgggt ccatggtgtc                              30
```

METHOD FOR PRODUCING HIGHLY ACTIVE CELLOBIOHYDROLASE AND HIGHLY ACTIVE CELLOBIOHYDROLASE

BACKGROUND OF THE INVENTION

Field of the Invention

The present invention relates to a saccharifying enzyme for biorefinery applications. In particular, the present invention relates to a method for producing cellobiohydrolase with improved activity, and cellobiohydrolase with high activity.

Description of the Related Art

Various modifications of proteins have been performed using transgenic techniques. Also for enzymes, attempts to improve the enzyme activity such as enhancement in activity or increase in expression level have been made. As a method for enhancing the enzyme activity, a method of modifying an amino acid, introducing a mutation into the amino acid at the active center where an enzyme binds to a substrate, and selecting a highly active enzyme has been employed.

In many instances, the substrate binding site of an enzyme is exemplified by a key and a keyhole. Meanwhile, some of enzymes that act on a polymer substrate such as cellulose are known to have a relatively long substrate binding site with a tunnel shape or a groove shape into which the polymer substrate is fitted, though they are limited to only a part of the enzymes.

Exoglucanase that is an enzyme configured to cut the cellulose chain at the end produces cellobiose as a reaction product, and is called cellobiohydrolase. In the case of cellobiohydrolase, the active center has a tunnel shape, as described above, and the cellobiose cut by the enzyme reaction leaves from the opposite side of the tunnel. Therefore, the enzyme reaction proceeds without the cellobiohydrolase separating from the cellulose chain.

Attempts to improve the enzyme activity of cellobiohydrolase have been made in the past, and several mutants have been already reported. For example, a mutant relating to *Talaromyces* (see the specification of U.S. Pat. No. 8,790,894) and a mutant of cellobiohydrolase derived from *Phanerochaete* (see Japanese Patent Laid-Open No. 2010-046034) are known.

SUMMARY OF THE INVENTION

However, enzymes with higher efficiency have been desired in the field of biorefinery, and the aforementioned conventional arts lack a sufficient effect of improving the activity. Accordingly, it is required to produce a cellobiohydrolase mutant with higher activity.

Further, a processive enzyme that catalyzes a reaction while holding the polymer substrate like cellobiohydrolase has a substrate binding site extending over a wide range. Therefore, the effects of many amino acids remain unstudied. Accordingly, it is an object of the present invention to obtain cellobiohydrolase with higher activity by investigating substitutional effects at the sites of unstudied amino acids.

A method for producing cellobiohydrolase with improved activity of the present invention includes: substituting, with alanine, asparagine that is an amino acid at position 62 from an N-terminal of cellobiohydrolase shown in SEQ ID NO: 1, or asparagine at a position corresponding to the position 62 in an amino acid sequence of cellobiohydrolase having homology with the cellobiohydrolase shown in SEQ ID NO: 1.

As a result of analysis by alanine scanning, which is one way to specify a site that affects protein functions, cellobiohydrolase with high activity could be obtained by substituting asparagine that is the amino acid at position 62 of cellobiohydrolase shown in SEQ ID NO: 1 with alanine. This amino acid residue is located within the tunnel structure of the cellobiohydrolase.

Accordingly, it is presumed that, when cellobiohydrolase has homology with the cellobiohydrolase shown in SEQ ID NO: 1, cellobiohydrolase with high activity would be obtained likewise by substituting asparagine at an equivalent position to the position 62 with alanine.

Further, cellobiohydrolase with improved activity of the present invention includes: a mutation by substitution, with alanine, of asparagine that is an amino acid at position 62 from an N-terminal of cellobiohydrolase shown in SEQ ID NO: 1, or asparagine at a position corresponding to the position 62 in an amino acid sequence of cellobiohydrolase having homology with the cellobiohydrolase shown in SEQ ID NO: 1.

The cellobiohydrolase in which the asparagine at position 62 in the sequence shown in SEQ ID NO: 1 is substituted with alanine has high activity. Accordingly, cellobiohydrolase with higher activity can be obtained by combination with a mutant obtained by substituting asparagine at position 62 or asparagine at a position corresponding to the position 62 with alanine, or an amino acid substitution that includes such substitution and that is known to strengthen the enzyme activity.

The cellobiohydrolase with improved activity of the present invention has a sequence shown in SEQ ID NO: 2. The cellobiohydrolase shown in SEQ ID NO: 2 has specific activity 12 times that of a wild type enzyme.

DETAILED DESCRIPTION OF THE PREFERRED EMBODIMENTS

The crystal structure of cellobiohydrolase has been already known. A site where cellobiohydrolase interacts with cellulose as a substrate is surrounded by a long loop, which is called a tunnel structure. The active center which binds to the cellulose and where a degradation reaction occurs is located within the tunnel structure. Accordingly, a highly active mutant is considered to be obtained by obtaining an enzyme having a mutation of an amino acid within the tunnel structure.

However, since the tunnel structure extends over a wide range, it is difficult to analyze all the amino acids that affect the activity by binding to the substrate. Therefore, amino acids that are predicted to be inside the tunnel structure based on the three-dimensional structure, and that may highly possibly affect the activity by inhibiting the movement of cellulose as the substrate are selected to be analyzed by alanine scanning. First, in order to introduce a mutation, a cellobiohydrolase gene was isolated, and a vector for expression in *Aspergillus oryzae* was constructed.

(1) Construction of Vector that Expresses Cellobiohydrolase in *Aspergillus oryzae*

(Genomic DNA Extraction of *Acremonium cellulolyticus*)

*Acremonium cellulolyticus* strain H1 (FERM BP-11508, which will be hereinafter abbreviated as "strain H1") was inoculated on a PDB agar medium (a plate medium obtained by adding 1.5% (mass/volume) agarose to a PDA medium (BD Difco, PDA broth)) and was cultured at 30° C. for one week. The obtained fungi were cut out together with the agar to a diameter of 5 mm and were inoculated on the PDA medium, followed by shaking culture at 30° C. and 130 rpm. The resultant culture was centrifuged at 15,000 rpm for 10 minutes, thereby recovering the fungi. Further, washing of the recovered fungi with the PDA medium was repeated twice to obtain a fungal sample.

Beads were placed in a 2 mL plastic tube containing the fungal sample, and were subjected to milling by a desktop bead mill (Shake Master, manufactured by Bio Medical Science) for 90 seconds three times, thereby allowing the fungal sample to be in powder form. Thereafter, DNA was extracted using Nucleon (manufactured by Amersham plc).

(DNA Cloning of Wild Type Cellobiohydrolase of *Acremonium cellulolyticus*)

Using primers 1 and 2 shown in SEQ ID NOS: 3 and 4 (see Table 1) and using the obtained genomic DNA as a template, the sequence encoding wild type cellobiohydrolase was amplified by PCR. As DNA polymerase, KOD-plus (manufactured by TOYOBO CO., LTD.) was used. After one cycle of PCR at 94° C. for 2 minutes was performed, 30 cycles of PCR at 96° C. for 20 seconds, subsequently at 60° C. for 30 seconds, and further at 72° C. for 5 minutes were performed. The obtained PCR product was purified using a QIAquick PCR purification kit (manufactured by Qiagen N.V.). The amino acid sequence of the obtained wild type cellobiohydrolase of *Acremonium cellulolyticus* is shown in SEQ ID NO: 1.

even in the presence of nitric acid are introduced. A preparation method will be briefly described below.

First, plasmids into which the genes of nitrate reductase gene niaD derived from *Aspergillus oryzae* are incorporated are constructed. *Aspergillus oryzae* RIB40 strain (NBRC number: 100959, which will be hereinafter abbreviated as "RIB40 strain") was obtained from the National Institute of Technology and Evaluation. Using primers 3 and 4 shown in SEQ ID NOS: 5 and 6 and using the genomic DNA of RIB40 strain as a template, DNA of nitrate reductase gene niaD was amplified by PCR.

The amplified niaD DNA was purified by digestion with AvaI and NdeI, which was thereafter inserted into the AvaI and NdeI sites of pBR322 to construct pBR-niaD.

Then, the terminator region of agdA gene derived from *Aspergillus oryzae* was incorporated into pBR-niaD.

Using primers 5 and 6 shown in SEQ ID NOS: 7 and 8 and using the genomic DNA of RIB40 strain as a template, DNA in the terminator region of agdA gene derived from *Aspergillus oryzae* (which may be hereinafter referred to as "agdA terminator") was amplified by PCR.

The obtained PCR-amplified product was digested with restriction enzymes SalI and AvaI, and the digested product was inserted into the SalI and AvaI sites of pBR-niaD to obtain plasmid pBR-agdAT-niaD.

Then, the promoter region of enoA gene derived from *Aspergillus oryzae* was incorporated into the obtained pBR-agdAT-niaD.

Using primers 7 and 8 shown in SEQ ID NOS: 9 and 10 and using the genomic DNA of RIB40 strain as a template, DNA in the promoter region of enoA gene derived from *Aspergillus oryzae* (which may be hereinafter referred to as "enoA promoter") was amplified by PCR.

The obtained PCR-amplified product was digested with restriction enzymes NheI and SalI, which was inserted into the NheI and SalI sites of pBR-agdAT-niaD to obtain plasmid pBR-enoAP-agdAT-niaD.

TABLE 1

| Primer number | Nucleotide sequence 5'→3' | SEQ ID NO: | Remarks |
|---|---|---|---|
| 1 | tcctccaagt tacccatgtc tgccttgaac tctttc | 3 | Cellobiohydrolase |
| 2 | cgcttcgtcg acccoctaca aacattgaga gtagtaaggg | 4 | Cellobiohydrolase |
| 3 | atgctcggga gctttggatt tcctacgtct tc | 5 | niaD |
| 4 | atgcatatgt cgagagtgtt gtgtgggtca acg | 6 | niaD |
| 5 | atggtcgacg aagcgtaaca ggatagccta gac | 7 | agdA Terminator |
| 6 | atgcccgaga gtaacccatt cccggttctc tag | 8 | agdA Terminator |
| 7 | atggctagca gatctcgcgg cagggttgac | 9 | enoA Promoter |
| 8 | atggtcgacc ccgggtaact tggaggacgg aagaaaagag | 10 | enoA Promoter |

(Preparation of pBR-enoAP-agdAT-niaD)

A vector, pBR-enoAP-agdAT-niaD, in which nitrate reductase gene niaD derived from *Aspergillus oryzae*, the terminator region of agdA gene derived from *Aspergillus oryzae*, and the promoter region of enoA gene derived from *Aspergillus oryzae* are incorporated into *Escherichia coli* plasmid, pBR322, was produced. Expression of the nitrate reductase gene niaD makes it possible to select fungi into which plasmids that enable the growth of *Aspergillus oryzae*

(Incorporation of Wild Type Cellobiohydrolase DNA into pBR-enoAP-agdAT-niaD)

The pBR-enoAP-agdAT-niaD was digested with a restriction enzyme SmaI to obtain SmaI restriction fragment of pBRenoAP-agdAT-niaD.

The sequence encoding wild type cellobiohydrolase was cloned into the SmaI fragment using an In-Fusion (R) HD Cloning Kit (manufactured by Clontech Laboratories, Inc.) to obtain plasmid pBR-enoAP-CBH-agdAT-niaD (vector for CBH expression in *Aspergillus oryzae*).

(Incorporation of Mutant Cellobiohydrolase DNA into pBR-enoAP-agdAT-niaD)

Mutant cellobiohydrolase was produced by PCR of two fragments, one of which is from the 5' end of cellobiohydrolase gene to the mutation site and the other of which is from the mutation site to the 3' end of the gene. The construction was achieved by incorporating the obtained two fragments of DNA into pBR-enoAP-agdAT-niaD. At this time, since the primer containing the mutation site is designed to anneal, the mutant cellobiohydrolase gene is continuous from the 5' end to the 3' end while having the same amino acid sequence as the wild type cellobiohydrolase except for having the mutation site when it is incorporated into pBR-enoAP-agdAT-niaD.

Example 1

Production of Alanine Substitution Mutants

Based on the three-dimensional structure of cellobiohydrolase of *Acremonium cellulolyticus*, amino acids at 30 sites located within the tunnel structure of cellobiohydrolase derived from acremonium having the amino acid sequence shown in SEQ ID NO: 1 were substituted with alanine, and the activity was analyzed to select amino acids that lead to an improvement in enzyme activity. Of the 30 sites of substitution, activity improvement as compared to wild type cellobiohydrolase was seen in 6 sites.

An improvement, even if slight, in the activity by alanine substitution was seen in lysine (K) at position 203, asparagine (N) at position 62, asparagine at position 125, aspartic acid (D) at position 201, arginine (R) at position 289, and aspartic acid at position 281 of the amino acid sequence shown in SEQ ID NO: 1 (the mutants may be respectively referred to as K203A, N062A, N125A, D201A, R289A, and D281A depending on the substituted amino acids and their positions).

Figure 1:
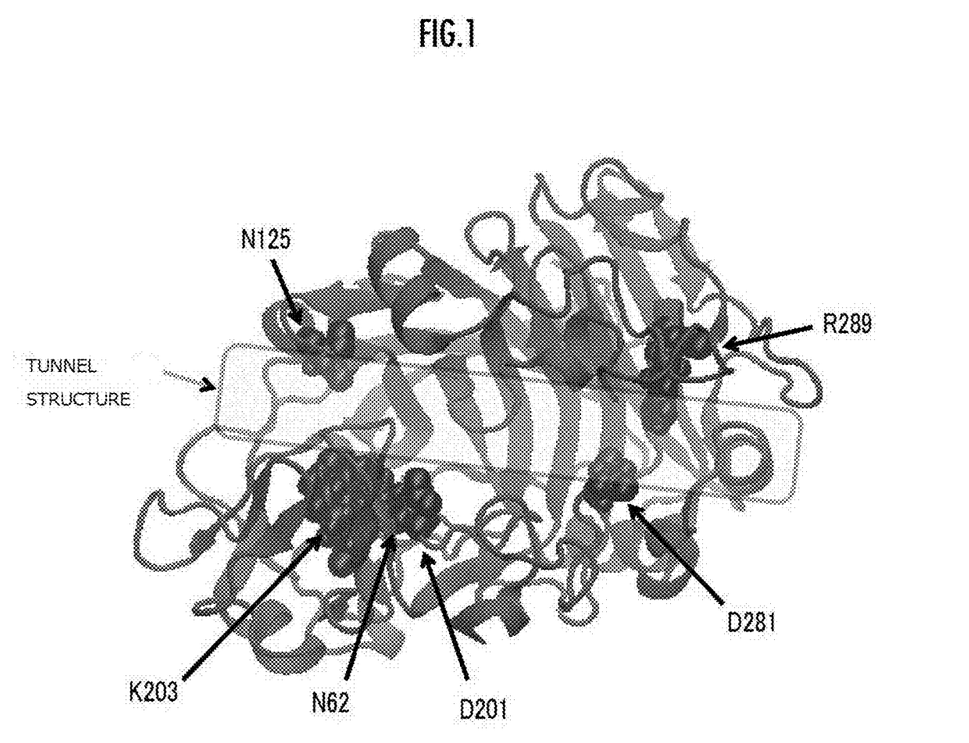
FIG. 1 is a view schematically showing the three-dimensional structure of cellobiohydrolase and showing the respective positions of amino acid residues.

FIG. 1 shows the three-dimensional structure of cellobiohydrolase of *Acremonium cellulolyticus* obtained from The Rutgers/UC San Diego/San Diego Supercomputer Center Protein Data Bank (RCSB PDB), and the positions of the aforementioned amino acids that showed an improvement in the activity by alanine substitution. The sites that showed an improvement in the activity by alanine substitution exist over the total length of the tunnel structure.

Table 2 below shows the primers used for producing the aforementioned six mutants. PCR was performed in the same manner as the amplification of the genomic DNA of wild type cellobiohydrolase except that primer 1 used for cloning cellobiohydrolase and primers 9 to 14, and primers 15 to 20 and primer 2 used for cloning cellobiohydrolase described above were used as the respective primer pairs.

TABLE 2

| Primer number | Nucleotide sequence 5'→3' | SEQ ID NO: | Remarks |
| --- | --- | --- | --- |
| 9 | gatgaaggcc aagtcacgag ggcattgaga | 11 | K203A |
| 10 | acgccaggcg gcatctaacg taatggcacc | 12 | N062A |
| 11 | tccgacggcg gaaccggtaa cgaagttcag | 13 | N125A |
| 12 | cttcaaggca cgagggcatt gagagtcaca | 14 | D201A |
| 13 | accaagggcg taagggttga agtcacatcc | 15 | R289A |
| 14 | acatccggca gggtcgcagg taccggcgta | 16 | D281A |
| 15 | gacttggcct tcatcgctgg tcaggccaac | 17 | K203A |
| 16 | gatgccgcct ggcgttgggt ccatggtgtc | 18 | N062A |
| 17 | ggttccgccg tcggatctcg tacttacctg | 19 | N125A |
| 18 | cctcgtgcct tgaagttcat cgctggtcag | 20 | D201A |
| 19 | ccttacgccc ttggtgtcac tgacttctac | 21 | R289A |
| 20 | gaccctgccg gatgtgactt caacccttac | 22 | D281A |

(Production of Transformants of *Aspergillus oryzae* by Introduction of Vectors for Wild Type and Mutant Cellobiohydrolase eExpression in *Aspergillus oryzae*)

*Aspergillus oryzae* niaD300 strain (niaD deficient strain, obtained from the National Research Institute of Brewing) was transformed with the plasmid pBR-enoAP-CBH-agdAT-niaD into which the aforementioned wild type cellobiohydrolase was incorporated or a plasmid into which a mutation was introduced, by the conventional PEG-calcium method (Mol. Gen. Genet., vol. 218, p. 99 to 104, 1989). The strains which could grow in the Czapek-Dox medium (3% (mass/volume) dextrin, 0.1% (mass/volume) potassium dihydrogenphosphate, 0.2% (mass/volume) potassium chloride, 0.05% (mass/volume) magnesium sulfate, 0.001% (mass/volume) iron sulfate, and 0.3% (mass/volume) sodium nitrate) was selected to obtain transformants (wild type and mutant cellobiohydrolase-transformed *Aspergillus oryzae* strains).

(Preparation of Cellobiohydrolase)

The produced cellobiohydrolase-transformed *Aspergillus oryzae* strains were sporulated in the Czapek-Dox medium, and spores were recovered using sterile water. The spores were inoculated into 100 mL of a PD liquid medium (2% (mass/volume) dextrin, 1% (mass/volume) polypeptone, 0.1% (mass/volume) casamino acid, 0.5% (mass/volume) potassium dihydrogenphosphate, 0.05% (mass/volume) magnesium sulfate, and 0.1% (mass/volume) sodium nitrate) contained in a 500 mL erlenmeyer flask to a final spore concentration of $1 \times 10^4$/mL. By liquid culture at 30° C.

for three days, cellobiohydrolase or cellobiohydrolase having an amino acid mutation was expressed and secreted in the medium. The culture liquid after the culture was used as an enzyme sample. The enzyme sample was investigated by SDS-PAGE analysis, and protein quantitation was conducted thereon for use.

(Measurement of Cellulolytic Activity)

As a reactive substrate, microcrystalline cellulose (manufactured by Merck KGaA) was used. Further, a standard curve was created from the measured values of 4-point dilution series (0.5 to 5.0 mM) prepared by appropriately diluting a 10 mM (mmol/L) glucose solution with a 200 mM acetate buffer (pH 5.5).

First, 40 µL of the 200 mM acetate buffer (pH 5.5) and 50 µL, of a 4% (mass/volume) microcrystalline cellulose suspension suspended in the 200 mM acetate buffer were added to a 1.5 mL plastic tube, and they were sufficiently mixed. Thereafter, the temperature thereof was adjusted to 50° C.

Figure 2:
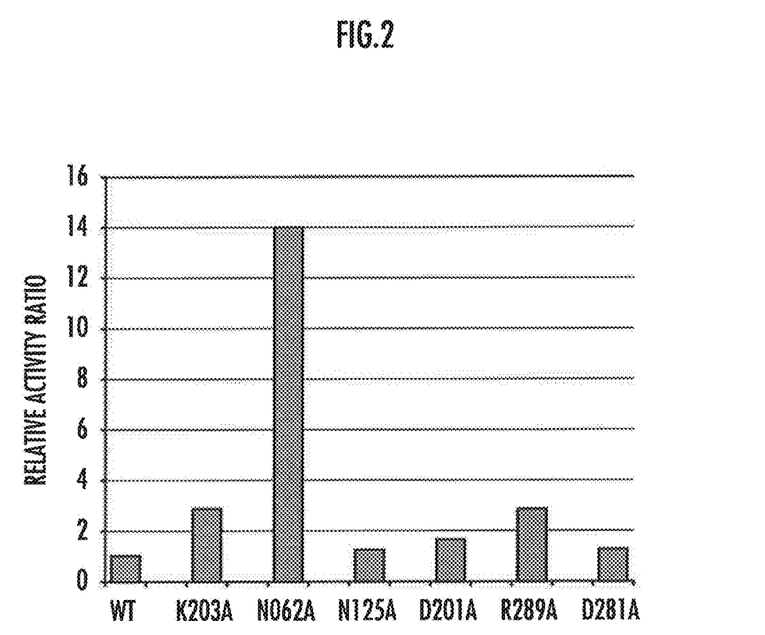
FIG. 2 is a graph showing a relative activity ratio of mutants of cellobiohydrolase to the wild type by alanine scanning.

Subsequently, 10 µL of wild type or each mutant (K203A, N062A, N125A, D201A, R289A, or D281A) cellobiohydrolase aqueous solution was added to the tube, thereby starting an enzyme reaction. After a lapse of one hour from the start of the reaction, 100 µL of a DNSA (1.6% (mass/volume) sodium hydroxide, 0.5% (mass/volume) 3,5 dinitrosalicylic acid, and 30% (mass/volume) potassium sodium tartrate tetrahydrate) solution was added thereto and mixed, thereby stopping the reaction. After the reaction was stopped, the mixture was centrifuged (at 15,000×g for 5 minutes), and the supernatant was boiled at 100° C. for 5 minutes, followed by cooling in ice. Thereafter, 100 µL of the reaction solution was separated from the tube, and the absorbance at 540 nm ($A_{540}$) of the solution diluted with 100 µL of distilled water was measured. As a blank, a similarly treated sample to which a 20 mM acetate buffer was added instead of the enzyme sample was used. A cellulolytic activity value per unit weight of the enzyme was obtained by calculating a glucose concentration from the measured value of $A_{540}$ and the standard curve, and dividing it by an enzyme concentration obtained by the protein quantitation. FIG. 2 shows the results.

FIG. 2 shows the results for mutants K203A, N062A, N125A, D201A, R289A, and D281A having improved activity as compared to wild type (WT). In particular, the mutant N062A obtained by substituting asparagine (N) at position 62 with alanine (A) had a specific activity 14 times that of wild type cellobiohydrolase. This activity is significantly high also as compared to the cellobiohydrolase mutants disclosed in the related arts.

Example 2

Based on the fact that the mutant N062A obtained by substituting asparagine (N) at position 62 with alanine (A) had improved activity as compared to wild type, the amino acid at position 62 was substituted with amino acids having different properties such as hydrophobicity, acidity, and alkalinity, and its activity was measured.

Table 3 below shows primers used for the production. PCR was performed in the same manner as the amplification of the genomic DNA of wild type cellobiohydrolase except that primer 1 used for cloning the aforementioned cellobiohydrolase and primers 21 to 27, and primers 28 to 34 and primer 2 used for cloning cellobiohydrolase were used as the respective primer pairs.

TABLE 3

| Primer number | Nucleotide sequence 5'→3' | SEQ ID NO: | Remarks |
|---|---|---|---|
| 21 | acgccaccag gcatctaacg taatggcacc | 23 | N062W |
| 22 | acgccagacg gcatctaacg taatggcacc | 24 | N062V |
| 23 | acgccaggag gcatctaacg taatggcacc | 25 | N062S |
| 24 | acgccactgg gcatctaacg taatggcacc | 26 | N062Q |
| 25 | acgccactcg gcatctaacg taatggcacc | 27 | N062E |
| 26 | acgccacttg gcatctaacg taatggcacc | 28 | N062K |
| 27 | acgccaatgg gcatctaacg taatggcacc | 29 | N062H |
| 28 | gatgcctggt ggcgttgggt ccatggtgtc | 30 | N062W |
| 29 | gatgccgtct ggcgttgggt ccatggtgtc | 31 | N062V |
| 30 | gatgcctcct ggcgttgggt ccatggtgtc | 32 | N062S |
| 31 | gatgcccagt ggcgttgggt ccatggtgtc | 33 | N062Q |
| 32 | gatgccgagt ggcgttgggt ccatggtgtc | 34 | N062E |
| 33 | gatgccaagt ggcgttgggt ccatggtgtc | 35 | N062K |
| 34 | gatgcccatt ggcgttgggt ccatggtgtc | 36 | N062H |

After plasmids were constructed, cellobiohydrolase-transformed *Aspergillus oryzae* strains were obtained and mutant enzymes were obtained, in the same manner as in Example 1. Then, the corn stover degrading activity was measured.

(Measurement of Corn Stover Degrading Activity)

After a saccharification pretreatment was performed by mixing a 2.5% (mass/mass) sulfuric acid aqueous solution with finely milled rice straws as lignocellulosic biomass to a mass ratio of 1:10 and maintaining the mixture at a temperature of 150° C. for 10 minutes, the pH was adjusted to 5.8 using a sodium hydroxide aqueous solution, followed by drying at 50° C. for one day. Thereafter, the resultant after being finely crushed using a hammer was used as a reactive substrate for activity measurement.

In the activity measurement, 80 μL of a 200 mM acetate buffer (pH 5.5) and 100 μL of a 4% (mass/volume) corn stover suspension suspended with the 200 mM acetate buffer were added to a 1.5 mL plastic tube, and they were sufficiently mixed. Thereafter, the temperature thereof was adjusted to 50° C.

Figure 3:
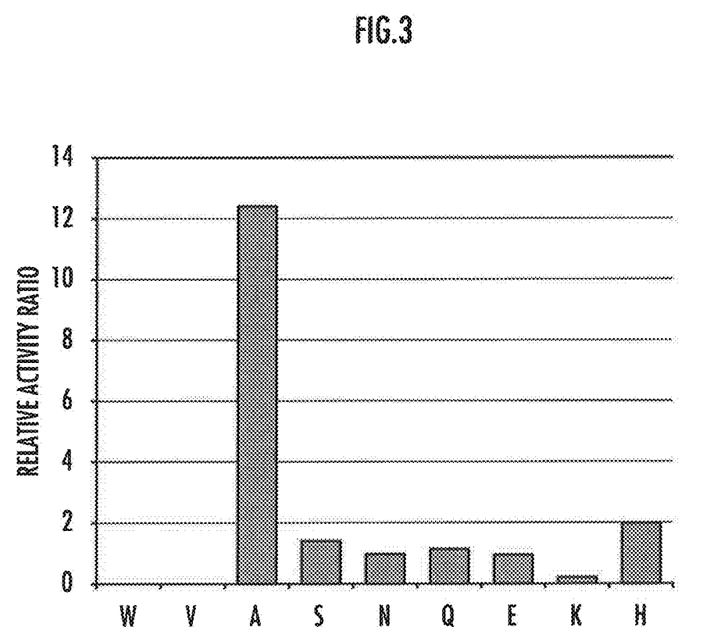
FIG. 3 is a graph showing the relative activity ratio to the wild type, when the amino acid at position 62 from the N-terminal is substituted.

Subsequently, 20 μL of wild type or each mutant cellobiohydrolase aqueous solution was added thereto to start an enzyme reaction. After a lapse of one hour from the start of the reaction, the mixture was centrifuged at 15,000×g and 4° C. for 5 minutes. The obtained supernatant was transferred into a new 1.5 mL plastic tube, followed by heat treatment at 95° C. for 5 minutes. Thereafter, the supernatant was centrifuged at 15,000×g and 4° C. for 5 minutes. The resultant supernatant was transferred into a new 1.5 mL plastic tube, and thereafter was filtered with a 0.2 μm (13 mm disk) filter. A 0.2 mL filtrate was transferred into a vial, and cellobiose was detected by HPLC measurement. As a standard substance, cellobiose manufactured by Wako Pure Chemical Industries, Ltd. was used, and the sugar concentration was evaluated. In the HPLC measurement, Waters 2695 (manufactured by Nihon Waters K.K.) as a separator, Waters 2414 (manufactured by Nihon Waters K.K.) as an RI detector, and Bio-rad HPX-87H (Bio-Rad Laboratories, Inc.) as a column were used. The measurement was performed using ultrapure water as an eluent in the conditions of a flow rate of 0.6 mL/min, a column temperature of 80° C., and a detector temperature of 40° C. FIG. 3 shows the results.

An improvement in activity was observed in alanine (A), glutamine (Q), histidine (H) as compared to wild type (asparagine (N)). Alanine had a specific activity 12 times or more that of the wild type (N) even in the case where saccharification was determined with the substrate changed to corn stover.

Substitution with amino acids having various properties, including hydrophobic amino acids (tryptophan (W) and valine (V)), neutral amino acids (serine (S) and glutamine (Q)), an acidic amino acid (glutamic acid (E)), and basic amino acids (lysine (K) and histidine (H)) was performed, but none of them could show a greater improvement in the activity than the improvement by alanine substitution.

As a reason why the activity was improved by the substitution with alanine, it is inferred that the steric hindrance when cellulose moves inside the tunnel structure is removed. It is expected that mutants having higher activity would be obtained by further substitution with other mutations that were found to show an improvement in the activity in the present invention, such as lysine at position 203 and arginine at position 289 together with alanine, in addition to the substitution of asparagine at position 62 with alanine.

As shown in Examples 1 and 2, the cellobiohydrolase mutant in which asparagine at position 62 defined in SEQ ID NO: 2 is substituted with alanine has higher activity as compared to wild type cellobiohydrolase.

Cellobiohydrolase is an enzyme classified as GH7 of a glycoside hydrolase family. In enzymes belonging to GH7, amino acids located in a tunnel structure are very well conserved across species. Actually, also in *Trichoderma reesei* and *Phanerochaete chrysosporium*, the amino acid at a position corresponding to position 62 in SEQ ID NO: 1 is asparagine. Accordingly, it is expected that enzymes with improved activity are obtained by changing asparagine at this position to alanine, not only in cellobiohydrolase shown in SEQ ID NO: 1, but also in cellobiohydrolase shown in homologous amino acid sequences.

Further, since the tunnel structure is conserved across species, a further improvement in the activity can be expected by introducing other amino acid mutations that have been reported to improve the cellobiohydrolase activity in addition.

What is claimed is:

1. A method for producing cellobiohydrolase with improved activity, comprising:
substituting asparagine 62 of the cellobiohydrolase as shown in SEQ ID NO: 1 with alanine, or an asparagine positioned corresponding to said asparagine 62 in an amino acid sequence of an *Acremonium cellulolyticus* cellobiohydrolase with alanine.

* * * * *